(12) United States Patent
Arnesen

(10) Patent No.: US 9,848,110 B2
(45) Date of Patent: Dec. 19, 2017

(54) INSPECTION SCOPE DEVICES AND METHODS FOR MOBILE ELECTRONIC DEVICES

(71) Applicant: Gadget Support LLC, Tempe, AZ (US)

(72) Inventor: Niels Arnesen, Tempe, AZ (US)

(73) Assignee: Gadget Support LLC, Tempe, AZ (US)

( * ) Notice: Subject to any disclaimer, the term of this patent is extended or adjusted under 35 U.S.C. 154(b) by 0 days.

(21) Appl. No.: 14/617,410

(22) Filed: Feb. 9, 2015

(65) Prior Publication Data

US 2016/0050365 A1 Feb. 18, 2016

Related U.S. Application Data

(60) Provisional application No. 62/038,586, filed on Aug. 18, 2014, provisional application No. 62/080,682, filed on Nov. 17, 2014.

(51) Int. Cl.
| | | |
|---|---|---|
| *H04N 5/225* | (2006.01) | |
| *G01N 21/00* | (2006.01) | |
| *H04N 5/232* | (2006.01) | |

(52) U.S. Cl.
CPC ........... *H04N 5/2256* (2013.01); *G01N 21/00* (2013.01); *H04N 5/2252* (2013.01); *H04N 5/23212* (2013.01); *H04N 2005/2255* (2013.01)

(58) Field of Classification Search
None
See application file for complete search history.

(56) References Cited

U.S. PATENT DOCUMENTS

| | | | | |
|---|---|---|---|---|
| 8,451,328 | B2 * | 5/2013 | Yoshino | A61B 1/0638 348/222.1 |
| 2006/0215013 | A1 * | 9/2006 | Jongsma | A61B 1/00016 348/14.08 |
| 2008/0207996 | A1 * | 8/2008 | Tsai | A61B 1/00048 600/112 |
| 2012/0162401 | A1 * | 6/2012 | Melder | H04N 7/183 348/65 |
| 2013/0102359 | A1 * | 4/2013 | Ho | A61B 1/227 455/556.1 |
| 2014/0142390 | A1 * | 5/2014 | Bromwich | A61B 1/00126 600/160 |

OTHER PUBLICATIONS

Aardvark Waterproof Wireless Inspection Camera User Manual, Nov. 2013, Circuit Specialists.*
iBorescope 4 User's Manual, Sep. 10, 2014, General Tools & Instruments.*

* cited by examiner

*Primary Examiner* — Twyler Haskins
*Assistant Examiner* — Dwight C Tejano
(74) *Attorney, Agent, or Firm* — Snell & Wilmer L.L.P.

(57) ABSTRACT

Inspection scopes suitable for use in connection with mobile electronic devices are disclosed. The inspection scope may utilize an optical connection to the mobile electronic device and/or an electrical connection to the mobile electronic device. Software operative on the mobile electronic device is configured for control of inspection scope components and for acquisition of video and/or image data.

3 Claims, 11 Drawing Sheets

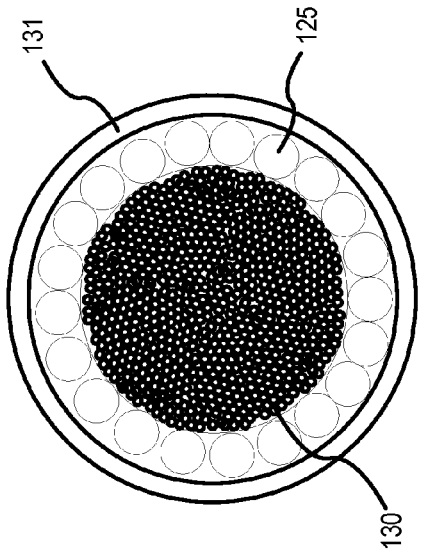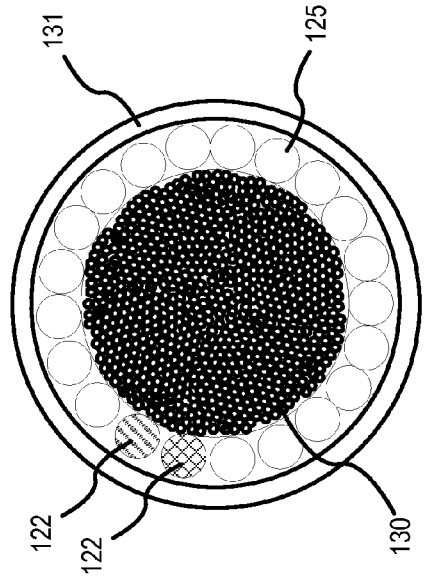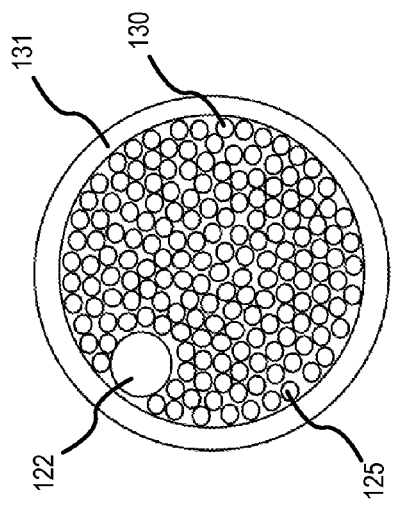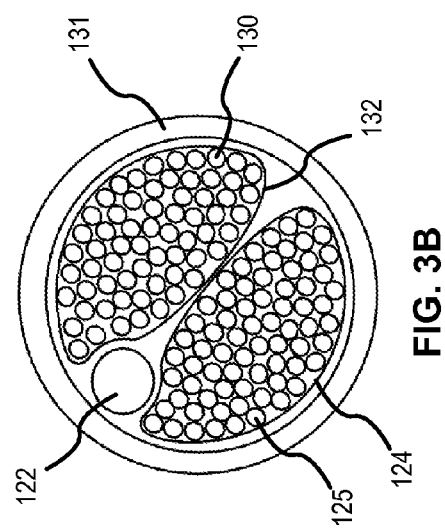

INSPECTION SCOPE DEVICES AND METHODS FOR MOBILE ELECTRONIC DEVICES

REFERENCE TO CO-PENDING APPLICATIONS

This application is a non-provisional of, and claims priority to, U.S. Provisional No. 62/038,586 filed on Aug. 18, 2014 and entitled "INSPECTION SCOPE FOR MOBILE ELECTRONIC DEVICES." This application is also a non-provisional of, and claims priority to, U.S. Provisional No. 62/080,682 filed on Nov. 17, 2014 and entitled "INSPECTION SCOPE FOR MOBILE ELECTRONIC DEVICES." The entire contents of all the foregoing applications are hereby incorporated by reference.

TECHNICAL FIELD

The present disclosure relates to inspection scopes and, in particular, to inspection scopes adapted for use with mobile electronic devices.

BACKGROUND

Mobile electronic devices, for example smartphones, are commonly used for image and video capture. However, mobile electronic devices may be too bulky to capture images and video in small or confined spaces. Further, a user may be precluded from capturing images or video in a location not reachable by the device user's hand, arm, or person. Accordingly, a device for enabling image and video capture by a mobile electronic device in small or remote spaces is desirable.

SUMMARY

In an exemplary embodiment, an inspection scope for a mobile electronic device comprises a lens component configured to acquire an image, an image guide component configured to transmit the image to an image capture component of a mobile device, and a mounting component configured to releasably couple the inspection scope to the mobile device.

In another exemplary embodiment, an inspection scope for a mobile electronic device comprises a camera component configured to acquire an image, an image cable configured to transmit the image acquired by the camera component to the mobile device, and a flexible tubing that at least partially surrounds the camera component and the image cable.

In another exemplary embodiment, a method of using an inspection scope for a mobile electronic device comprises coupling the inspection scope to the mobile electronic device, and opening an inspection scope application on a mobile device. The method further comprises focusing, via the inspection scope application, an image of a target area, and instructing, via the inspection scope application, the mobile electronic device to capture an image of the target area via a camera of the mobile electronic device.

The contents of this summary section are presented as a simplified introduction to the disclosure, and are not intended to be used to limit the scope of any claim.

BRIEF DESCRIPTION OF THE DRAWINGS

With reference to the following description and accompanying drawings:

FIGS. 3A through 3D illustrate cross-sections of exemplary inspection scopes in accordance with exemplary embodiments;

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the present disclosure.

For the sake of brevity, conventional techniques for image and/or video capture and transmission, inspection scope construction and use, fiber optics, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical inspection scope system.

Figure 1:
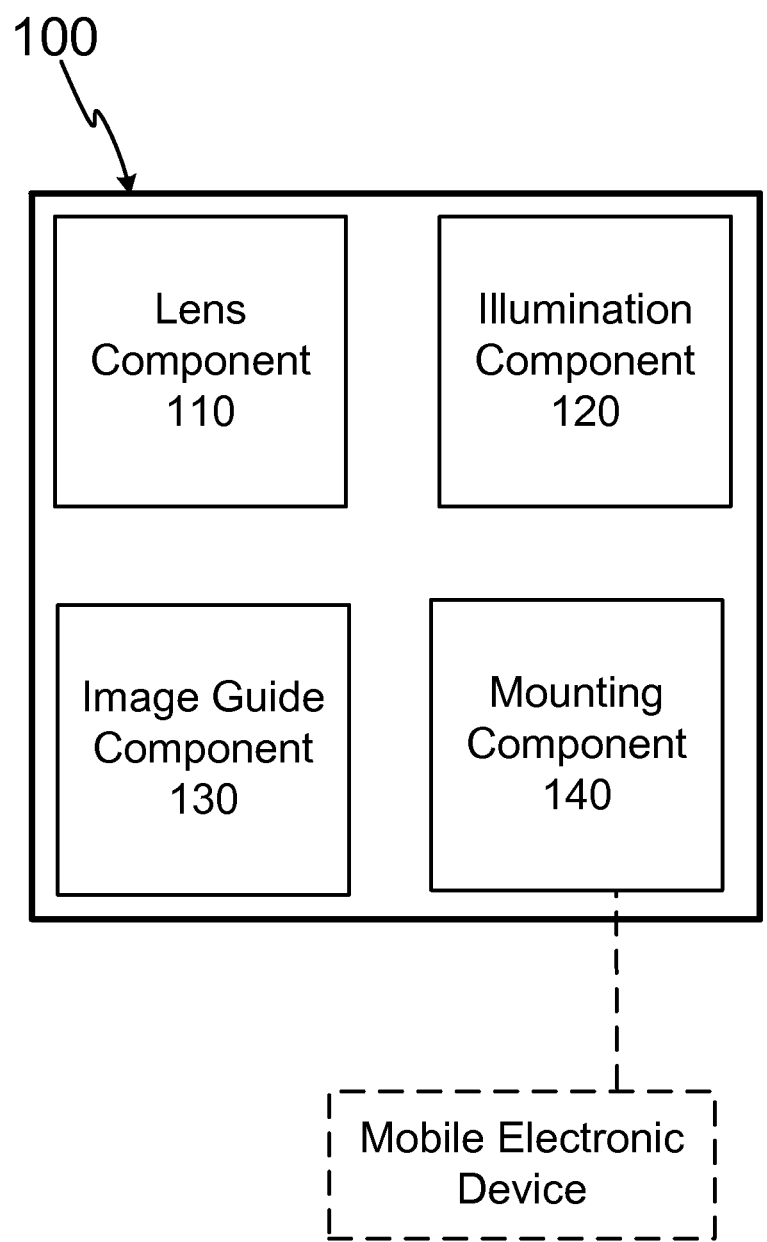
FIG. 1 illustrates a block diagram of an exemplary inspection scope in accordance with an exemplary embodiment.

With reference now to FIG. 1, in various exemplary embodiments an inspection scope 100 for mobile electronic devices comprises a lens component 110, an illumination component 120, an image guide component 130, and/or a mounting component 140. Lens component 110 is configured to collect and/or focus an image of an area of interest. Illumination component 120 is configured to deliver illumination to an area of interest. Image guide component 130 is configured to transmit, carry, and/or deliver an image of an area of interest to a mobile electronic device. Mounting component 140 is configured to physically, electronically, and/or optically couple inspection scope 100 to a mobile electronic device, for example a smartphone, tablet, notebook computer, and/or the like. Inspection scope 100 may also comprise various structural and/or supporting components, as suitable.

With reference now to FIGS. 2 through 5, in various exemplary embodiments inspection scope 100 is usable to capture moving and/or still images in locations inaccessible to a human eye, for example in tight, confined, and/or dark areas. Inspection scope 100 is configured to couple to a mobile electronic device so that the mobile electronic device can display and/or record the images or video. Inspection scope 100 is portable and flexible, and is configured to illuminate a target area for viewing. In various exemplary embodiments, inspection scope 100 may comprise a flexible tubing 131 that is positionable and has a sufficient length (for example, 18 inches, 24 inches, 36 inches, 48 inches, and/or the like) to allow a user to bend and/or position inspection scope 100 or a portion thereof, as desired. In various exemplary embodiments, flexible tubing 131 may be at least partially bifurcated, and the bifurcated portion may comprise an image guide tube 134 and an illumination tube 133.

In certain exemplary embodiments, lens component 110 is disposed at a capture end 111 of inspection scope 100. Lens component 110 comprises a single lens or compound lens configured to capture a coherent image and deliver the image to image guide component 130. Lens component 110 may be configured with a wide-angle, fisheye, or other suitable lens or lenses configured with a suitable focal length to allow wide-view inspection of a target area.

In various exemplary embodiments, image guide component 130 comprises one or more of glass, plastic, or similar optical fibers configured to transmit an image. Image guide component 130 may comprise one optical fiber or multiple optical fibers. In various exemplary embodiments, image guide component 130 may comprise between about 1,000 individual optical fibers and about 3,000 individual optical fibers coupled into a bundle. Moreover, image guide component 130 may comprise a suitable number of optical fibers in order to transmit an image to a mobile electronic device, while remaining flexible, bendable, positionable, and portable.

In various exemplary embodiments, image guide component 130 may be disposed at least partially within flexible tubing 131. Flexible tubing 131 may surround image guide component 130 at least partially between capture end 111 and mounting component 140. With reference now to FIG. 3B, image guide component 130 may be disposed at least partially within an image guide lumen 132. Image guide lumen 132 may be disposed at least partially within flexible tubing 131. Image guide lumen 132 may be configured to segregate image guide component 130 from other components of inspection scope 100 that may be disposed at least partially within flexible tubing 131. That being said, in accordance with various embodiments and with reference to FIG. 3A, image guide component 130 may be unsegregated from other components disposed within flexible tubing 131.

With reference now to FIGS. 3C and 3D, image guide component 130 may comprise a generally cylindrical bundle of optical fibers. In various exemplary embodiments, image guide component 130 may be configured with a diameter of between about 1.5 mm and about 2.5 mm, and preferably about 2 mm. That being said, image guide component 130 may have any diameter suitable for image transmission.

Figure 2:
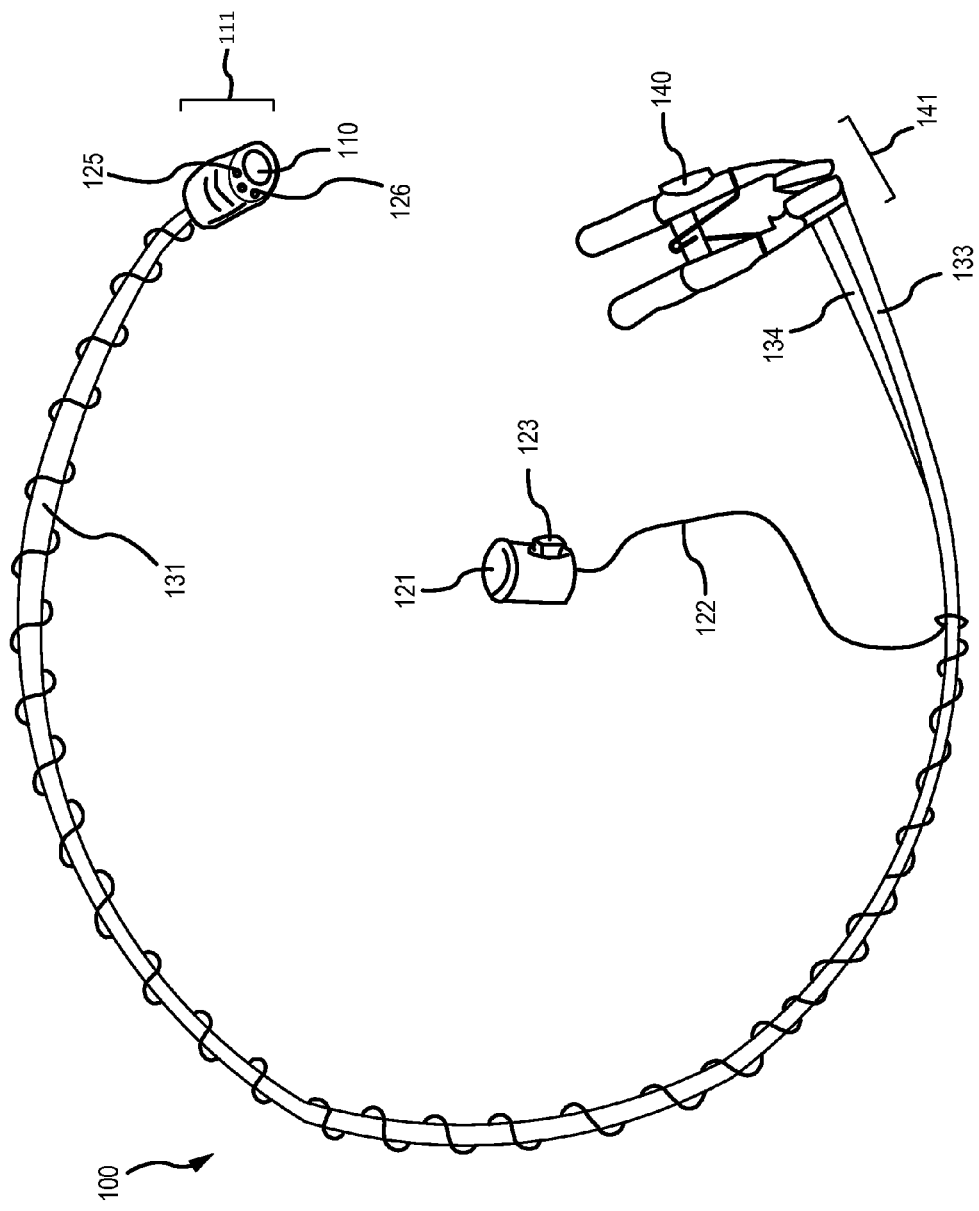
FIG. 2 illustrates an exemplary inspection scope in accordance with an exemplary embodiment.
Figure 5A:
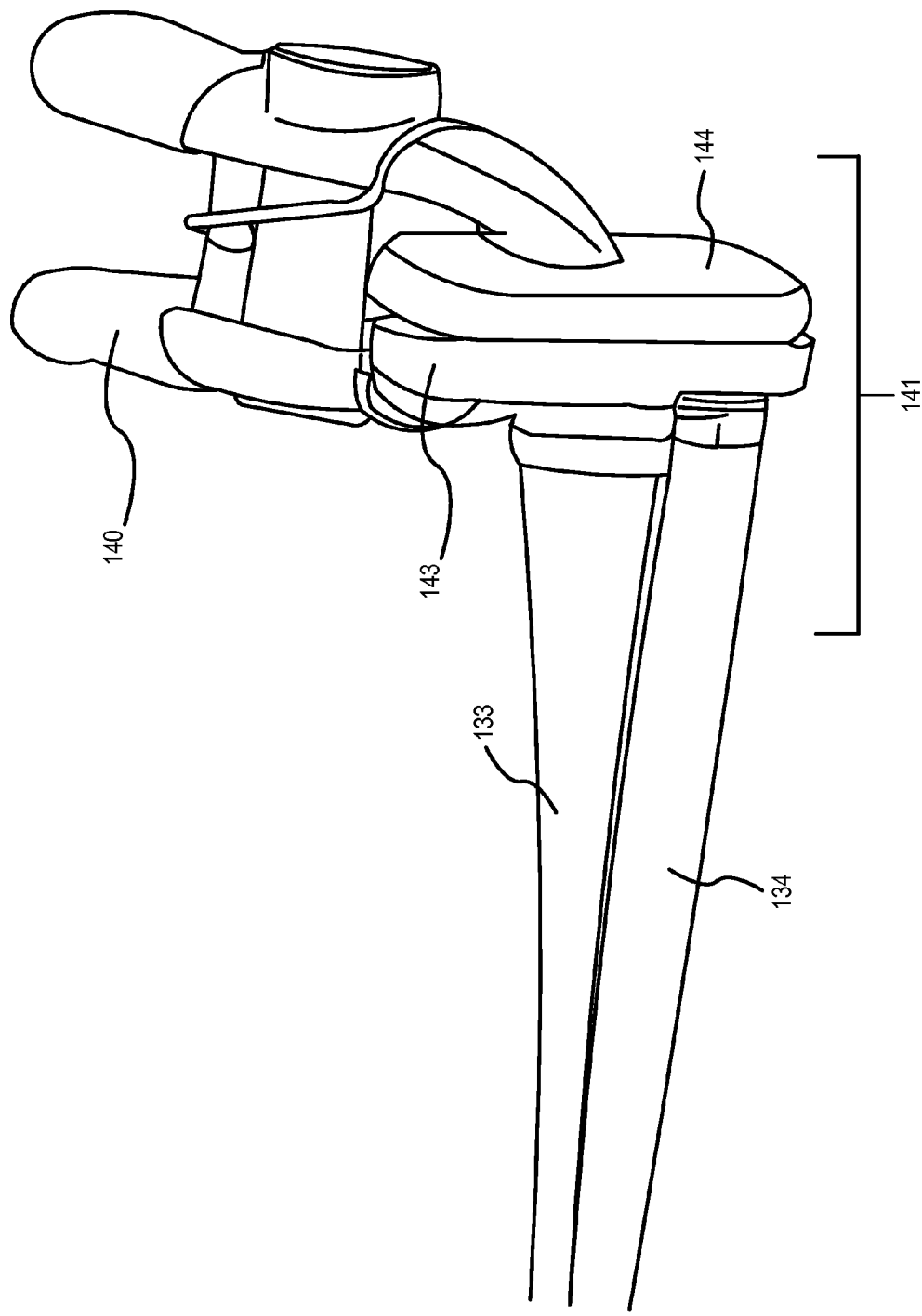
FIGS. 5A and 5B illustrate perspective views of exemplary inspection scope mounting ends in accordance with an exemplary embodiment.
Figure 5B:
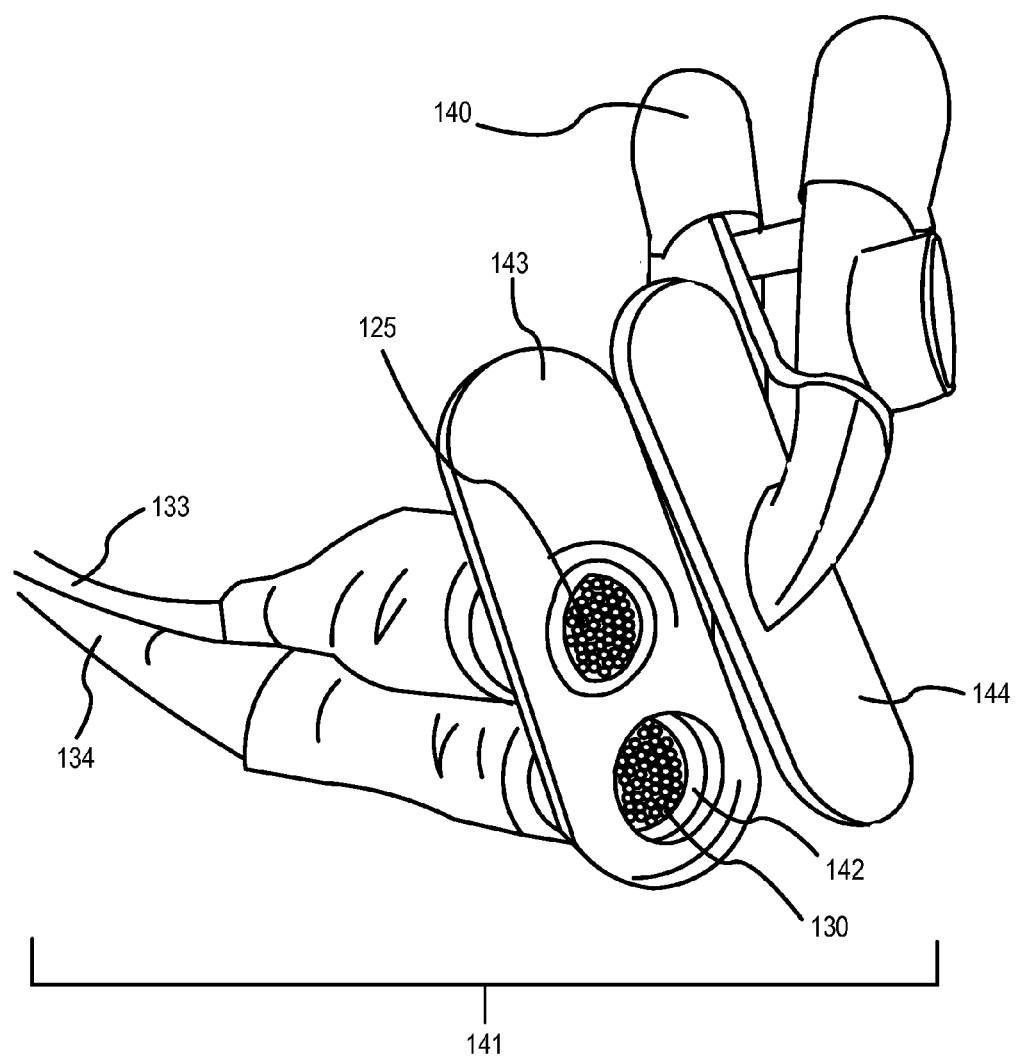

With reference now to FIGS. 2, 5A, and 5B, in various exemplary embodiments image guide component 130 may approach and/or abut a mobile electronic device at a mounting end 141 of inspection scope 100. At the mounting end 141, image guide component 130 may be configured with a mounting end lens 142. Mounting end lens 142 may comprise a magnifying, telescopic, and/or microscopic lens, and/or any other suitable lens or series of lenses. In this manner, images acquired via lens component 110 and delivered via image guide component 130 may be enlarged and/or modified such that the camera or other capture device of the mobile electronic device (or a human eye) can suitably acquire the image.

In various exemplary embodiments, illumination component 120 is configured to illuminate a target area. The target area may comprise an area external to inspection scope 100 of which lens component 110 is configured to capture an image. Exemplary target areas include confined spaces such as the interior of automobile engine compartments, cramped or inaccessible portions of buildings, and/or the like. If external light is sufficiently bright, illumination component 120 may be temporarily disabled.

In various exemplary embodiments, illumination component 120 may comprise at least one LED or other light-generating component 126 (for example, IR, visible, UV, and/or the like) disposed near lens component 110. In various embodiments, illumination component 120 may be powered via the mobile electronic device, for example via a USB port (micro, mini, USB 3.1 Type C, and/or the like), an Apple Lightning brand 9-pin connector, an Apple 30 pin connector, and/or the like, or other suitable interface for transmission of electrical power. Moreover, other components of inspection scope 100 (for example, configurable lenses, filters, etc.) may also be powered and/or controlled via the mobile electronic device. With reference again to FIG. 2, illumination component 120 may be powered via a battery 121 or other power source coupled to inspection scope 100.

Battery 121 may comprise a switch 123 configured to optionally enable or disable the flow of electrical current to light-generating component 126. Battery 121 may be electrically connected to light-generating component 126 by at least one electrical cable 122. Electrical cable 122 may be disposed externally from flexible tubing 131 or, as illustrated in FIGS. 3A, 3B, and 3D, may be disposed at least partially within flexible tubing 131. With reference now to FIG. 3D, electrical cables 122 may be disposed at least partially within flexible tubing 131 and around an outer circumference of image guide component 130. Electrical cables 122 are configured to transmit electrical current to light-generating component 126 and/or to other components of inspection scope 100.

In various exemplary embodiments, illumination component 120 may comprise a suitable number of optical fibers for illumination 125 disposed within flexible tubing 131, extending from mounting component 140 to capture end 111, and terminating near lens component 110. Optical fibers for illumination 125 may be configured for transmitting light from a mobile electronic device or component thereof (for example, from a flash LED associated with a camera of the mobile electronic device) to the capture end 111 of inspection scope 100 and toward the target area.

In various embodiments and with reference again to FIGS. 3B, 3C, and 3D, optical fibers for illumination 125 and optical fibers for imaging (for example, as comprising image guide component 130) may desirably be separated and/or adjustable with respect to one another in order to interface correctly with a variety of mobile electronic devices and/or in order to improve illumination of the target area. With reference now to FIG. 3B, optical fibers for illumination 125 may be disposed at least partially within an illumination lumen 124, which is disposed at least partially within flexible tubing 131. The illumination lumen 124 may be configured to segregate optical fibers for illumination 125 from other components of inspection scope 100 disposed at least partially within flexible tubing 131. That being said, in accordance with various embodiments and with reference to FIG. 3A, optical fibers for illumination 125 may be unsegregated from other components disposed within flexible tubing 131. With reference now to FIGS. 3C and 3D, optical fibers for illumination 125 may be disposed around an outer circumference of image guide component 130. In various exemplary embodiments, optical fibers for illumination 125 may be configured with a diameter of up to about 0.25 mm. That being said, optical fibers for illumination 125 may be configured with any diameter suitable for light transmission to the target area.

In inspection scope 100, mounting component 140 may be utilized to couple inspection scope 100 to a mobile electronic device. In various exemplary embodiments, mounting component 140 may comprise a clip or clips, a magnetic attachment, a snap-in or snap-on case or partial case specific to a mobile electronic device, and/or the like. With reference now to FIGS. 5A and 5B, in an exemplary embodiment mounting component 140 comprises a clamp having a first bracing portion 143 and a second bracing portion 144. The first bracing portion 143 comprises at least one aperture operatively coupled to flexible tubing 131 and configured to at least partially surround image guide component 130. In various embodiments, first bracing portion 143 may comprise a first aperture operatively coupled to image guide tube 134 and a second aperture operatively coupled to illumination tube 133. The first aperture may be configured to at least partially surround image guide component 130. The second aperture may be configured to at least partially surround optical fibers for illumination 125.

Figure 4A:
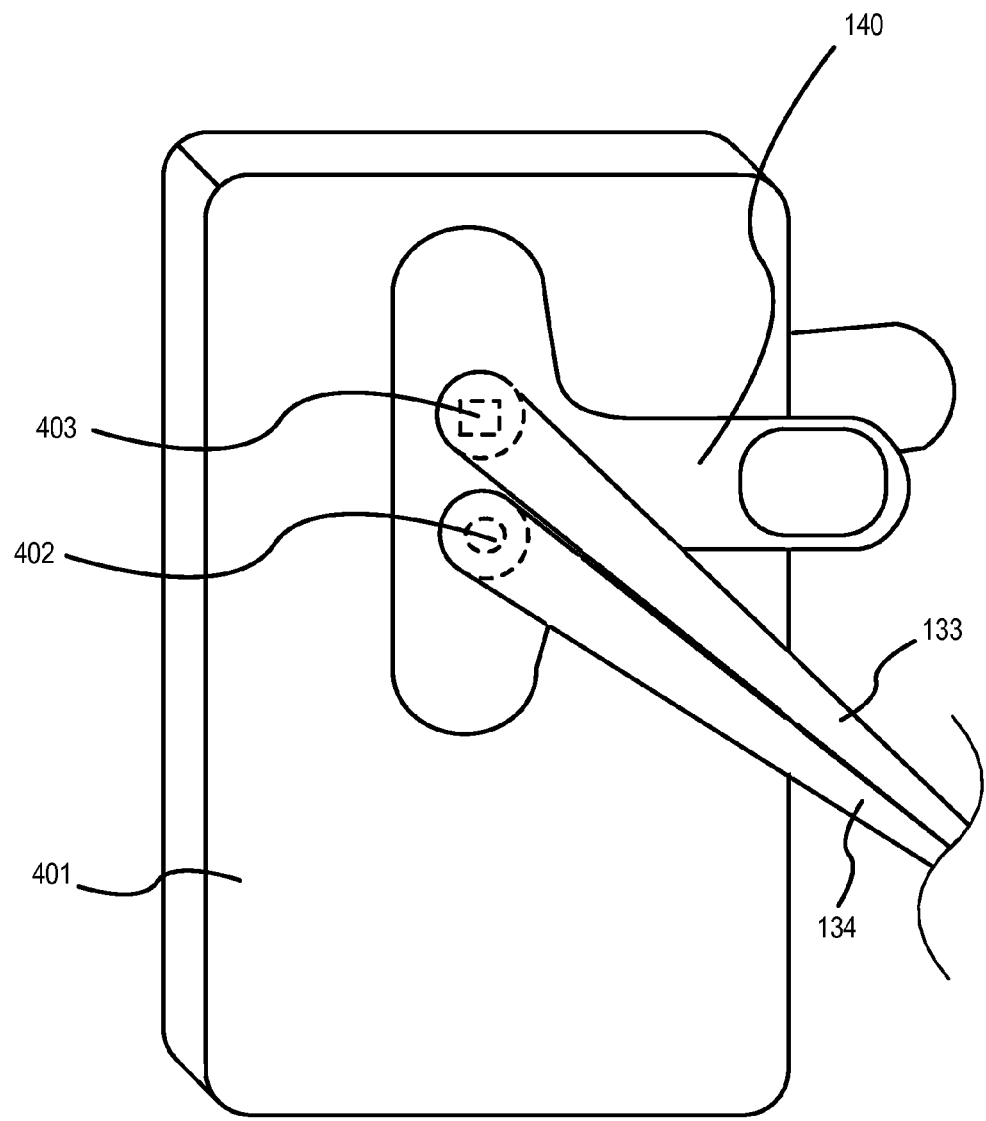
FIGS. 4A and 4B illustrate perspective views of exemplary inspection scopes coupled to mobile electronic devices in accordance with exemplary embodiments.
Figure 4B:
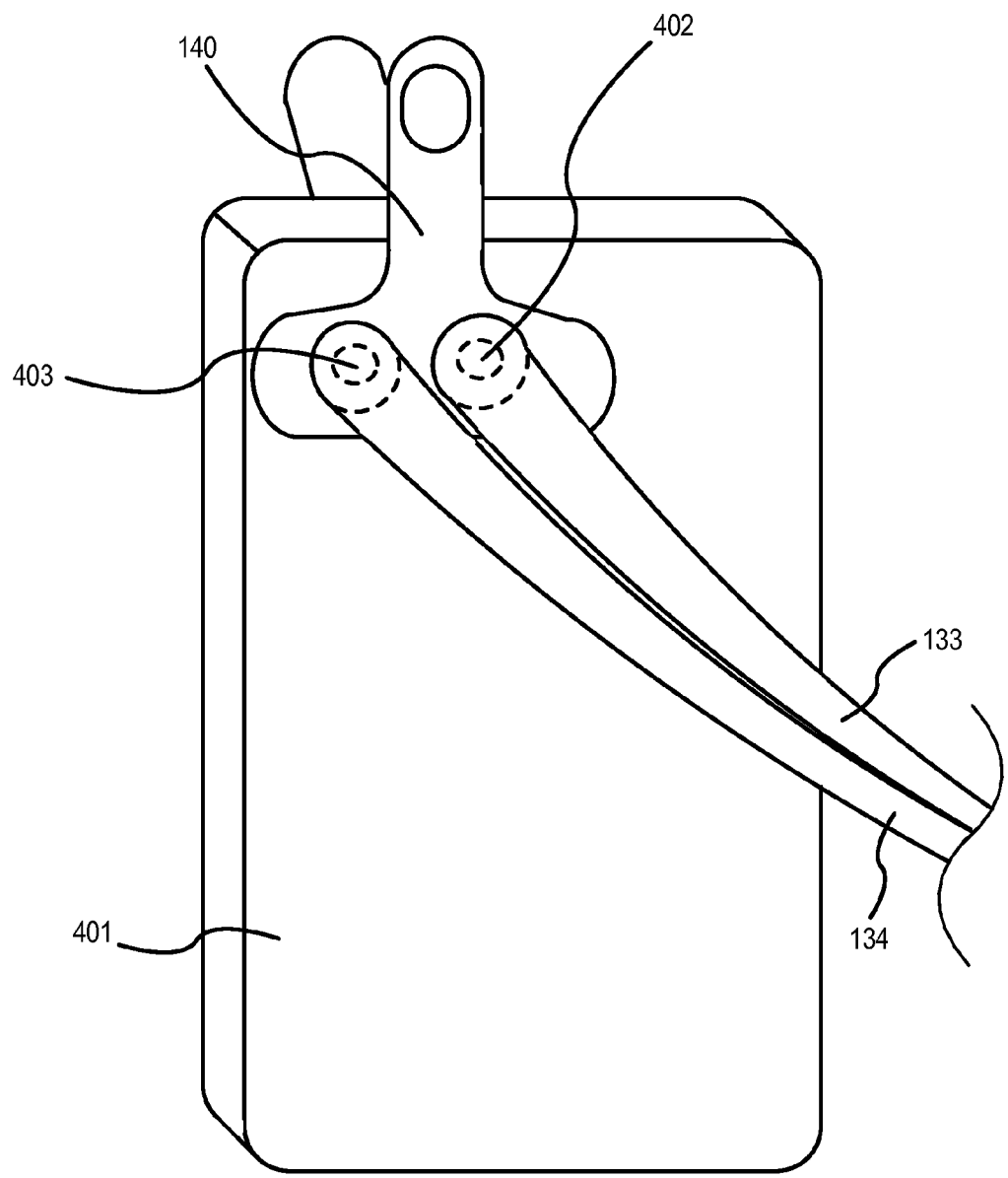

In various exemplary embodiments and with reference to FIGS. 4A and 4B, mounting component 140 is configured to releasably attach inspection scope 100 to a mobile electronic device 401. Mounting component 140 may be configured to align with the mobile electronic device 401 such that image guide tube 134, and image guide component 130 disposed therein, abut or are disposed adjacent to a camera 402 or other image capture device integrated in the mobile electronic device 401. Mounting component 140 may be configured to align with the mobile electronic device 401 such that illumination tube 133, and optical fibers for illumination 125 disposed therein, abut or are disposed adjacent to a light-generating device 403 integrated in the mobile electronic device 401.

In various exemplary embodiments, inspection scope 100 may be configured with manual and/or micro-focus components at the capture end 111 and/or at the mounting end 141. In this manner, inspection scope 100 may provide a suitable viewing and/or image capture result across multiple mobile electronic devices and/or in spite of environmental variations such as heat, cold, humidity, and/or the like.

In some embodiments, inspection scope 100 may be constructed with nonconductive materials. In this manner, inspection scope 100 may be suitable for use in electrically risky or otherwise hazardous areas. Additionally, inspection scope 100 may be configured with an image splitter in order to deliver images to multiple destinations simultaneously, for example to an eye and to a mobile electronic device.

In certain exemplary embodiments and with reference again to FIG. 2, inspection scope 100 may be configured with a focus block or focus guide. The focus block may be placed, for example, in the same focal plane as the termination of image guide component 130 at the capture end 111. The focus block may also be embedded in the termination of image guide component 130 at the capture end 111. In this manner, a mobile electronic device coupled to inspection scope 100 may more accurately focus or auto-focus on the termination of image guide component 130 in order to obtain an image of sufficient clarity and sharpness.

Figure 6:
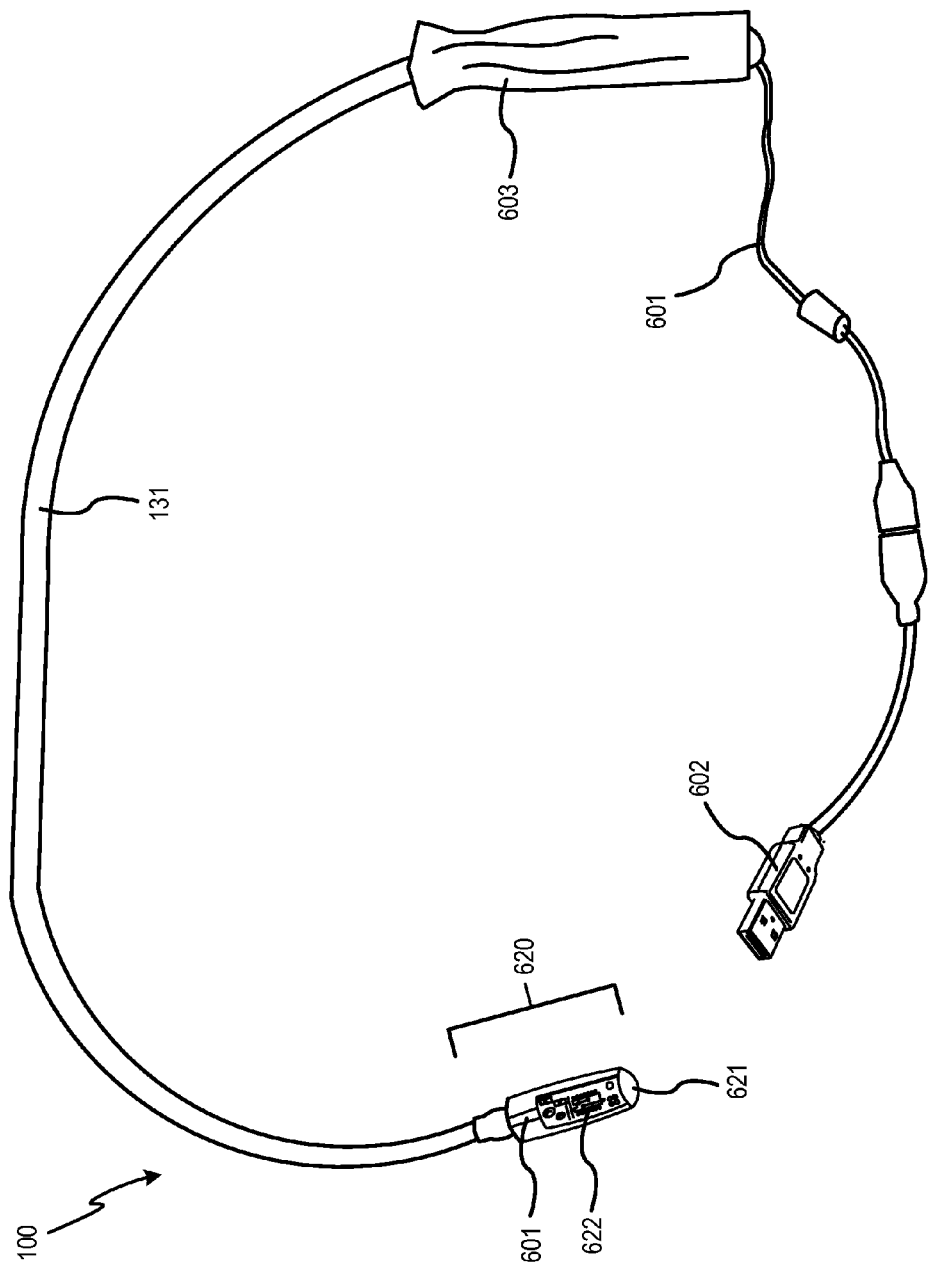
FIG. 6 illustrates components of an exemplary inspection scope electrically connectable to a mobile electronic device in accordance with an exemplary embodiment.
Figure 7A:
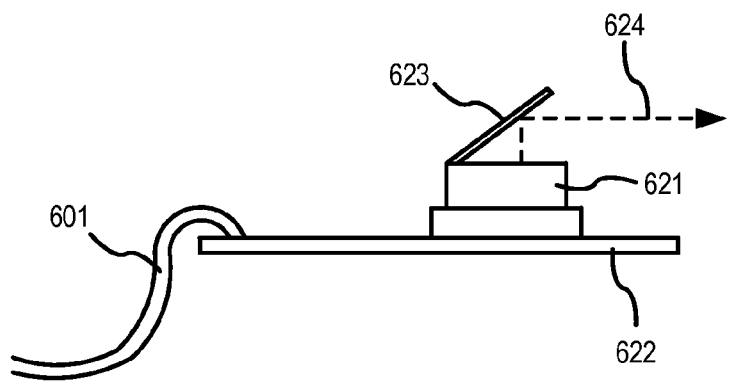
FIGS. 7A, 7B, and 7C illustrate components of exemplary inspection scopes electrically connectable to a mobile electronic device in accordance with exemplary embodiments.
Figure 7B:
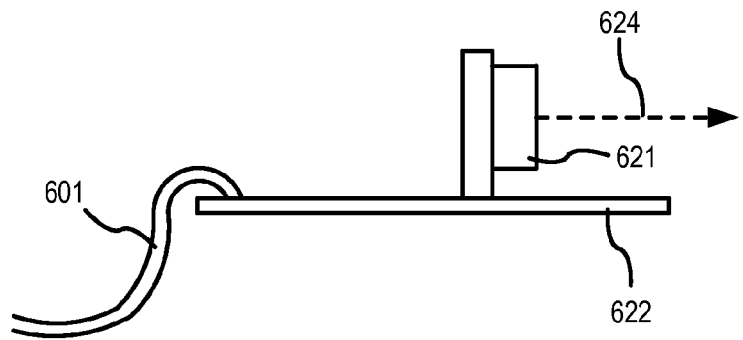
Figure 7C:
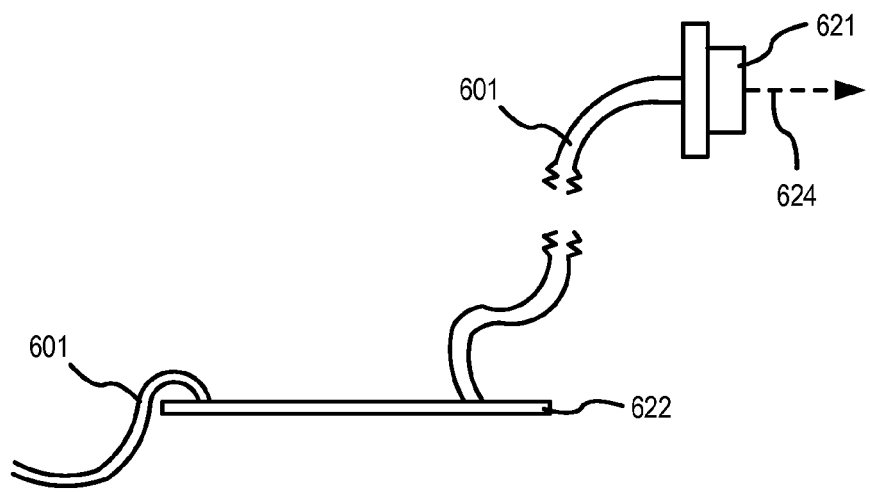
Figure 8:
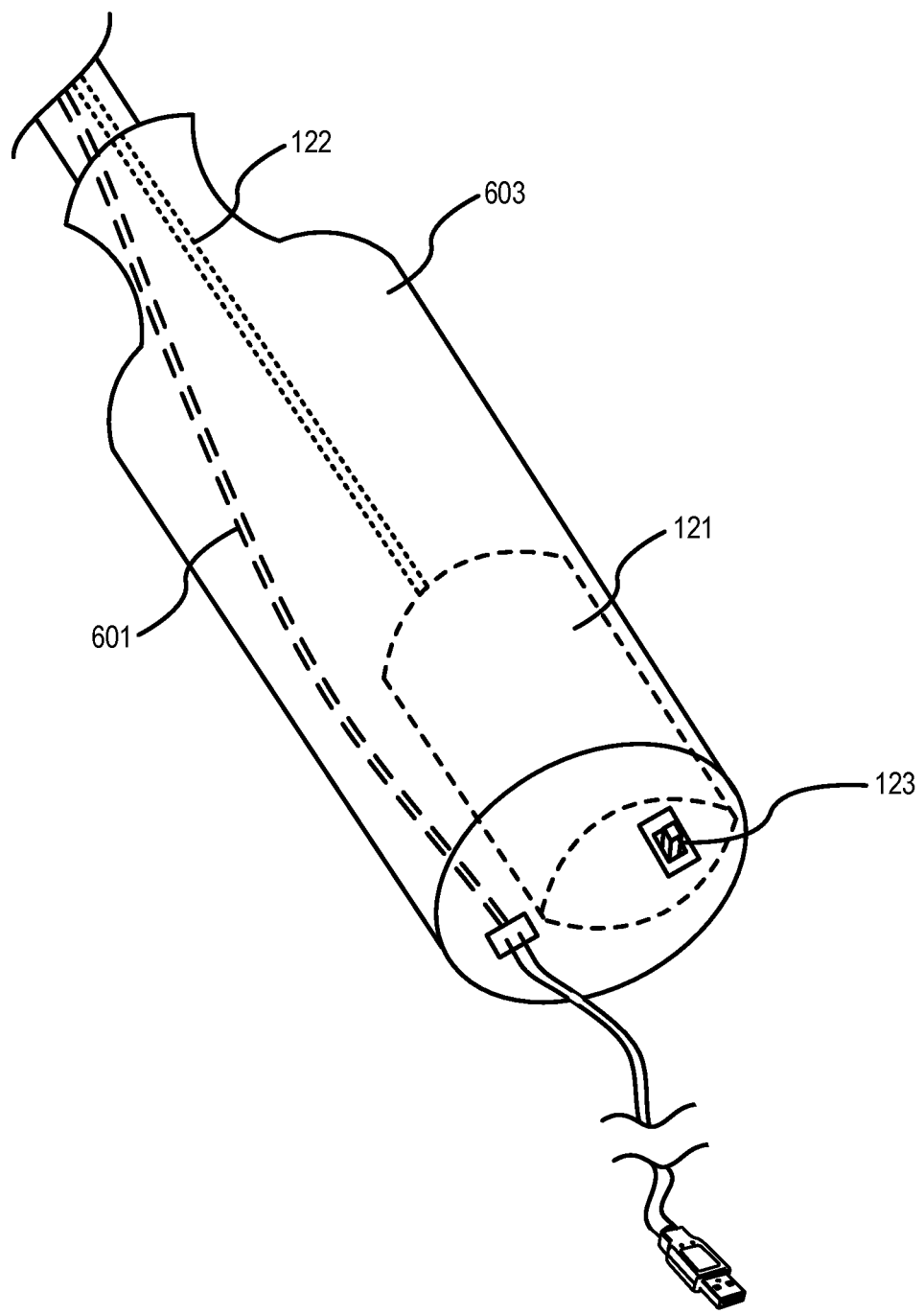
FIG. 8 illustrates handle components of an exemplary inspection scope electrically connectable to a mobile electronic device in accordance with an exemplary embodiment.

With reference now to FIGS. 6-8, in various exemplary embodiments, an inspection scope 100 may be configured to be electrically coupleable to other devices, for example a smartphone, tablet, or similar mobile electronic device. In these exemplary embodiments, image guide component 130 may be replaced with and/or supplemented by an image cable 601 configured to transmit an image acquired by a camera component 620 to the mobile electronic device. Stated differently, in various exemplary embodiments, flexible tubing 131 may be configured to at least partially surround camera component 620 and image cable 601. Image cable 601 may comprise an electrical connection suitable for conveying video information.

In various exemplary embodiments, inspection scope 100 is coupleable to a mobile electronic device via a Universal Serial Bus (USB) connection 602, such as a mini- or micro-USB connection. Additionally, inspection scope 100 may be coupleable to a mobile electronic device through an Apple brand 30-pin or 9-pin ("Lightning") connection. In general, inspection scope 100 may be coupleable to a mobile electronic device via any electrical connection suitable for transmission of video data.

With continuing reference to FIGS. 6-8, in certain exemplary embodiments camera component 620 may comprise a compact image sensor 621, such as a digital camera or the like, and a camera control electronics board 622. A viewing angle device 623, such as a micro mirror or prism, may be utilized to direct the view of the compact image sensor 621 in a desired direction. Configuration of the camera component 620 may be varied to achieve a desired form factor for the camera end of inspection scope 100.

In various exemplary embodiments and with reference to FIG. 7A, compact image sensor 621 may be physically and/or electrically coupled to camera control electronics board 622 and oriented such that a viewing angle 624 of the camera is perpendicular to the plane of the camera control electronics board 622. A viewing angle device 623 may be coupled to the compact image sensor 621 and oriented such that it reflects or refracts light, changing the direction of the viewing angle 624. The viewing angle device 623 may be configured such that the viewing angle 624 is oriented in the direction of a target area for viewing.

In certain exemplary embodiments and with reference to FIG. 7B, compact image sensor 621 may be physically and electrically coupled to camera control electronics board 622 and oriented such that a viewing angle 624 of the camera is parallel to the plane of the camera control electronics board 622, and therefore oriented in the direction of a target area for viewing.

In certain exemplary embodiments and with reference to FIG. 7C, compact image sensor 621 may be electrically coupled to, but physically separated from, camera control electronics board 622 in order to reduce the overall size of the camera component 620. Compact image sensor 621 may be oriented such that viewing angle 624 is oriented in the direction of a target area for viewing. Camera control electronics board 622 may be connected to the compact image sensor 621 and/or other components of inspection scope 100, for example via an image cable 601. Camera control electronics board 622 may be disposed in flexible tubing 131, in a handle 603 (with momentary reference to FIG. 6), or elsewhere in or on inspection scope 100.

In various exemplary embodiments, inspection scope 100 may include multiple, decouplable, sections of control cable. In this manner, the effective operational length of inspection scope 100 may be modified, as desired, by adding or removing control cable sections.

In certain exemplary embodiments, inspection scope 100 may be configured with wireless communication capabilities between the camera component 620 and an associated mobile electronic device. For example, the output signal of the camera component 620 may be transmitted to an associated mobile electronic device via Bluetooth, Wi-Fi, or other suitable radio communication protocols and/or hardware. Moreover, the associated mobile electronic device may send and receive control instructions, video data, and other exemplary electronic information to and from inspection scope 100 via wireless communication.

In various exemplary embodiments, the camera component 620 may be configured with further lenses, housings, and/or the like, as desired, in order to provide a desired field of view. In some exemplary embodiments, a fish-eye or wide angle lens is utilized in order to provide a wide field of view of the inspection area. However, any suitable lens or other image guide components may be utilized.

Camera component 620 may further comprise at least one light-generating component such as an LED. LEDs may provide visible, infrared, and/or ultraviolet illumination, as desired, in order to allow inspection at corresponding wavelengths. LEDs may be manually activated, for example via a switch, and/or may be electronically controlled, for example via an application installed on the mobile electronic device to which inspection scope 100 is coupled.

In various exemplary embodiments and with reference to FIGS. 6 and 8, inspection scope 100 may comprise a handle 603. The handle 603 can allow positioning of the camera component 620, and can facilitate ease of use by the user. Additionally, the handle 603 may at least partially surround camera control electronics board 622, battery 121, electrical cable 122, image cable 601, and/or other bulky or fragile components in order to reduce the size and/or increase the robustness of camera component 620.

FIG. 8 illustrates an exemplary handle, configured to contain a battery 121 to power various light-generating components, and provided with an on-off switch 123 therefor. In various exemplary embodiments, power for light generating components and other portions of inspection scope 100 may be drawn from the mobile electronic device via the electrical connection thereto.

In various exemplary embodiments, operation of inspection scope 100 may be controlled and/or facilitated via software, for example an application ("app") installed on the mobile electronic device to which inspection scope 100 is coupled. For example, LED illumination modes, camera configurations, and other aspects of inspection scope 100 operation may be controlled via the app. The app may also provide for image focusing, image capture, video recording, annotation, and the like.

Figure 9:
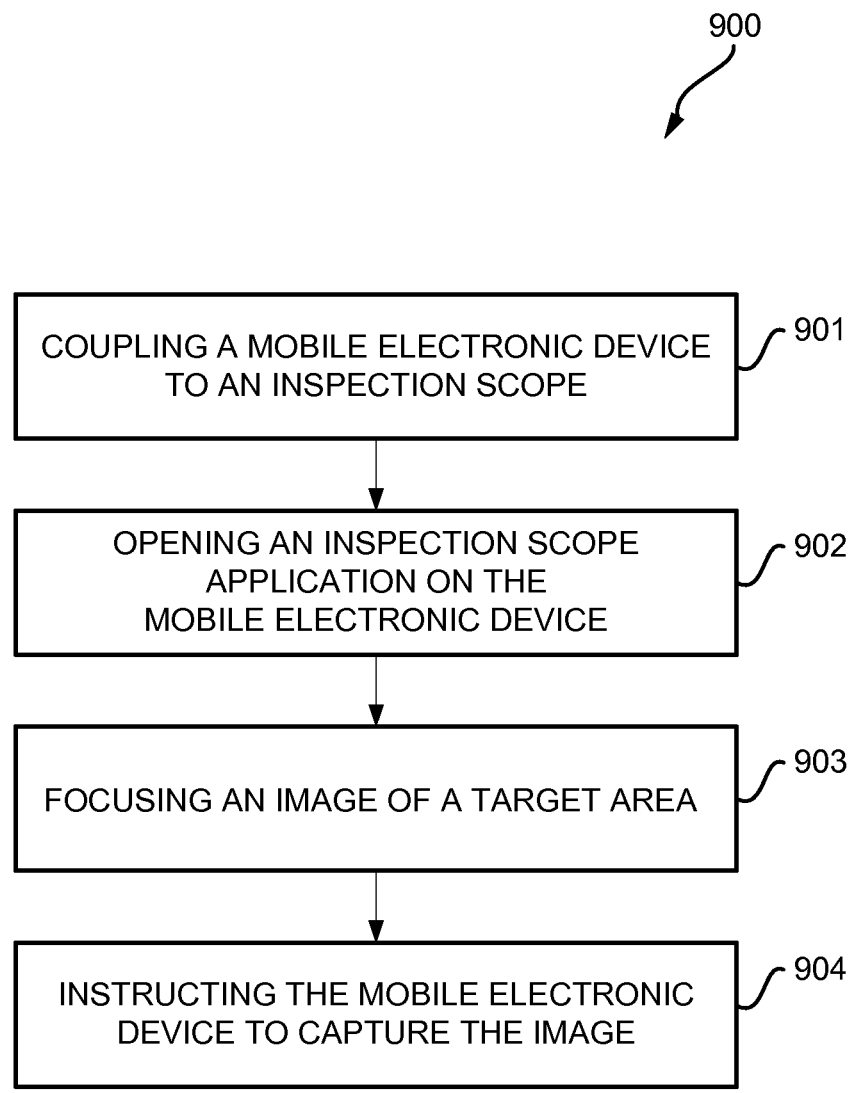
FIG. 9 illustrates a method of using an inspection scope in connection with a mobile electronic device in accordance with an exemplary embodiment.

In various exemplary embodiments and with reference now to FIG. 9, a method 900 for using an inspection scope in connection with a mobile electronic device comprises coupling the mobile electronic device to an inspection scope (step 901). Image capture may be controlled or facilitated by an app configured for operation in conjunction with the inspection scope. In various exemplary embodiments, method 900 may further comprise opening an inspection scope application on the mobile electronic device (step 902) and/or focusing an image of a target area of which the user desires to capture an image (step 903). In various embodiments, the app may perform, facilitate, or control the operations of focusing and capturing an image. The method may further comprise a user instructing the mobile electronic device to capture an image (step 904).

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection.

What is claimed is:

1. An inspection scope for a mobile electronic device, comprising:
    a lens component configured to acquire an image;
    an image guide component configured to transmit the image to an image capture component of the mobile electronic device, wherein the image guide component comprises a first set of optical fibers disposed within flexible, positionable tubing;
    a mounting component configured to releasably couple the inspection scope to the mobile electronic device, wherein the mounting component uses at least one of a clip, a magnetic attachment, a case specific to the mobile electronic device, or a clamp having a first bracing component and a second bracing component; and
    an illumination component configured to illuminate a target area where the image is acquired,
    wherein the illumination component comprises a second set of optical fibers disposed within the flexible positionable tubing and extending from the lens component to the mounting component,
    wherein each optical fiber in the first set of optical fibers is configured with a diameter smaller than the diameter of each optical fiber in the second set of optical fibers,
    wherein the second set of optical fibers are disposed in a continuous ring along the inside edge of the flexible positionable tubing, and wherein the first set of optical fibers are disposed entirely in the inner area of the ring formed by the second set of optical fibers.

2. The inspection scope of claim 1, further comprising a battery, wherein the battery is electrically coupled to a light-generating component.

3. The inspection scope of claim 1, wherein the flexible positionable tubing is at least partially bifurcated, the bifurcated portion comprising:
- an image guide tube containing the first set of optical fibers; and
- an illumination tube containing the second set of optical fibers.

\* \* \* \* \*